United States Patent [19]

Collingwood

[11] Patent Number: 4,566,332
[45] Date of Patent: Jan. 28, 1986

[54] WHEEL PROBE

[75] Inventor: John C. Collingwood, East Hagbourne, England

[73] Assignee: British Gas Corporation, London, England

[21] Appl. No.: 629,480

[22] Filed: Jul. 10, 1984

[30] Foreign Application Priority Data

Aug. 4, 1983 [GB] United Kingdom ............. 3321025

[51] Int. Cl.⁴ .............................................. G01N 29/04
[52] U.S. Cl. .......................................................... 73/639
[58] Field of Search ................. 73/638, 639, 637, 635, 73/640

[56] References Cited

U.S. PATENT DOCUMENTS 4,098,132  7/1978  Mikesell ....................... 73/639
4,302,976 12/1981  Bull .............................. 73/639

*Primary Examiner*—Howard A. Birmiel
*Attorney, Agent, or Firm*—Watson, Cole, Grindle & Watson

[57] ABSTRACT

A wheel probe for ultrasonically inspecting a component, such as the wall of a pipeline, is of hollow form to define a chamber in which an ultrasonic transducer is located. The transducer is supported by a mounting which occupies a major proportion of the chamber and comprises material for attenuating background noise in the wheel probe. The chamber is closed by an end member which also comprises material for attenuating background noise, while an elastomeric tire on the rim of the wheel probe extends over a portion of reduced diameter of the rim to attenuate unwanted ultrasound.

8 Claims, 1 Drawing Figure

U.S. Patent   Jan. 28, 1986   4,566,332
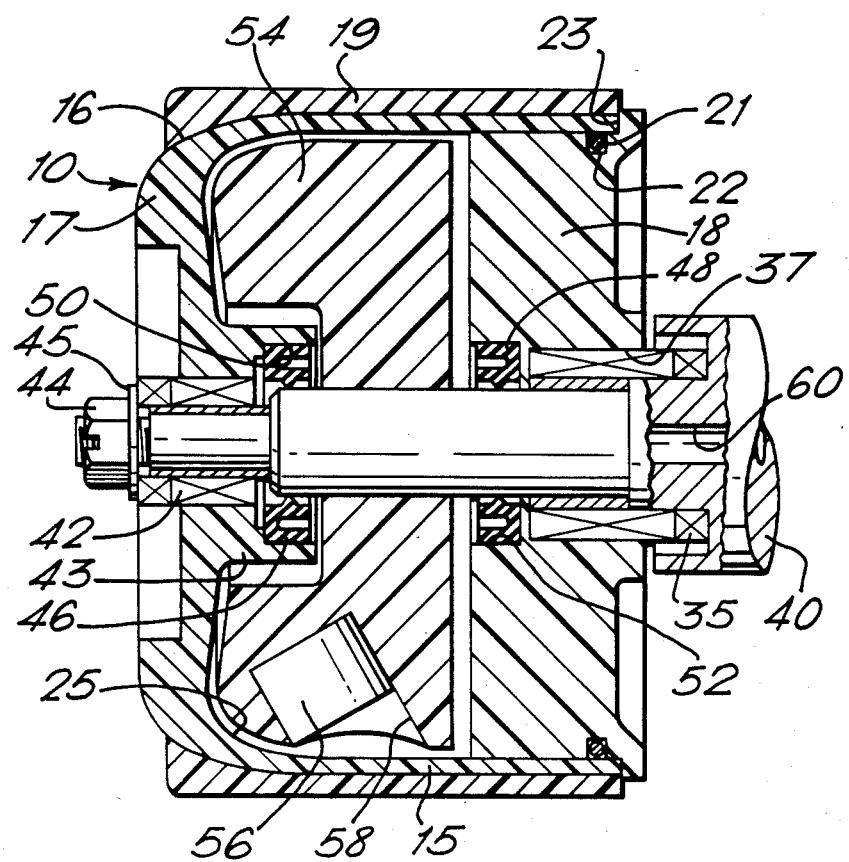

WHEEL PROBE

This invention relates to a wheel probe for ultrasonicaly inspecting a component such as the wall of a pipeline.

An example of such a wheel probe is described in British Patent Specification No. 2055201A (European patent application Publication No. 0023125A1) and comprises a hermetically sealed hollow wheel defining a chamber containing an acoustic coupling liquid and freely rotatable about a stationary mounting means which is also arranged to support an ultrasonic transducer for directing and receiving ultrasonic signals through the rim of the wheel. A disadvantage with probe wheels of this and other known kinds has been found to be the generation of unwanted spurious signals which give rise to ambiguous interpretation of the wanted defect-producing signals reflected from the component under test.

An object of the present invention is to provide an improved form of wheel probe less subject to the aforesaid disadvantage.

According to the present invention, a wheel probe of the kind described is characterised in that the mounting means includes an annular mounting member in which the transducer is supported comprising material for attenuating ultrasound and which is so shaped as to substantially fill the entire space of the chamber consistent with freedom of relative rotation for the wheel, thereby to inhibit unwanted ultrasound from reaching the transducer, the remaining small gap between the internal surfaces of the chamber and the mounting means being filled with the acoustic coupling liquid.

Desirably, the wheel comprises a cup-shaped body closable at least in part by an end member to define the chamber therein, and the end member comprises material for attenuating ultrasound. The end member may have an extended portion thereof adapted to locate inside the rim, and sealing means may be locatable between the rim and the extended portion of the end member.

The rim of the wheel may have a portion of reduced diameter to reduce the width of contact between the rim and the component, an elastomeric tire member about the rim extending along this portion to attenuate unwanted ultrasound.

It will be understood that the invention also includes an inspection vehicle for inspecting the wall of a pipeline, the vehicle having a plurality of the aforesaid wheel probes disposed therearound.

The invention will now be further described by way of example only with reference to the single FIGURE in the accompanying drawing which shows a view in medial section of a wheel probe.

Referring to the FIGURE, the wheel probe comprises a wheel 10 of circular form in diametral section, and comprises a cup-shaped nylon body having a rim 15 and a left hand side portion 17, the rim 15 having a portion at 16 of reduced diameter to reduce the effective width of the rim 15. A relatively thick, polycarbonate, plug member 18 has an 'O'-ring seal 21 in a circumferential groove 22, and locates in sealing engagement inside the rim 15 with a shoulder 23 of the plug member 18 abutting the rim 15, to define a chamber 25 inside the wheel 10. A solid polyurethane tire 19 locates about the rim 15 and extends along the portion 16. The wheel is mounted for rotation about a mounting means which includes a support member in the form of a stepped shaft 40.

The plug member 18 is mounted on a combined needle journal and ball thrust bearing 35 which projects into a housing 37 in the plug member 18. The bearing 35 is mounted on the shaft 40 which extends through the plug member 18 and provides at one end a mounting for a combined journal and ball thrust bearing 42 which locates in a boss 43 of the side portion 17. The bearing 42 is clamped on to the shaft 40 by a nut 44 and a washer 45 which thereby clamp the body and the plug member 18 together. Radial oil seals 46 and 48 locate in respective circular recesses 50, 52 in the boss 43 and the plug member 18 and bear circumferentially around the shaft 40 to retain an acoustic coupling liquid such as a mixture of glycerol and water in the chamber 25. The other end of the shaft 40 may be adapted to suit a mounting (not shown) to locate the wheel probe in an inspection vehicle (not shown), for example as described in the aforementioned British patent specification.

A polycarbonate, annular mounting member 54 is secured to the shaft 40 inside the chamber 25, and supports an ultrasonic transducer 56 in a cylindrical recess 58, a lead (not shown) from the transducer 56 extending through a hole 60 in the shaft 40 to a connection outside the wheel probe. The mounting 54 is shaped so that it substantially fills the chamber 25 and inhibits unwanted ultrasound from reaching the transducer 56.

In use, the wheel probe is moved along a component to be inspected, for example the wall of a pipeline, and the transducer 56 is fired to send a pulse of ultrasound into the component, the tire 19 coupling the ultasound into the component and vice versa. The transducer 56 then listens for ultrasonic signals reflected from defects in the component, with the extended portion of the tire 19 about the portion 16 of the rim 15, and the polycarbonate plug member 18, and the mounting 54 attenuating unwanted ultrasound in the wheel probe. The signals received by the transducer 56 result in an output from the transducer 56 which is subsequently amplified and analysed in a conventional manner.

The wheel probe therefore provides more effective damping as well as allowing a more compact wheel probe than hitherto, which can be an advantage in applications when a plurality of the wheel probes need to be assembled in an inspection vehicle, for example the inspection vehicle of the afore-mentioned patent specification.

Amplification of the output of the transducer 56 may be carried out by locating an amplifier (not shown) in the wheel probe itself close to the transducer 56, in order to improve the signal to noise ratio of the amplified output. However, if space limitations preclude the inclusion of the amplifier in the wheel probe, the amplifier may be located outside the wheel probe and connected to the lead from the transducer 56.

Although the use of polycarbonate material for the plug member 18 and mounting 54 is preferred because of its mechanical strength and capacity for attenuating ultrasound, alternative materials might be used, such as nylon or polythene for the mounting 54, or nylon for the plug member 18.

It will also be understood that particular features of known wheel probes, for example the wheel probe of the afore-mentioned British patent specification No. 2055201A may be incorporated where appropriate in the wheel probe of the invention.

I claim:

1. A wheel probe for ultrasonically inspecting a component, comprising a hollow wheel having spaced end walls and an annular wall defining a rim, the inner surfaces of the end walls and the rim defining a chamber containing an acoustic coupling liquid, stationary mounting means supporting the wheel for free rotation, the mounting means including an annular mounting member supporting an ultrasonic transducer for directing and receiving ultrasound through the rim of the wheel, the mounting member comprising material for attenuating sound, being located within the chamber so as to substantially fill the same and having end surfaces and an annular outer surface respectively spaced from the inner surfaces of the end walls and the rim so as to define a small gap therewith, thereby to inhibit ultrasound from reaching the transducer, the small gap being filled with the coupling liquid.

2. A wheel probe as claimed in claim 1, wherein the wheel comprises a cup-chaped body, one of the end walls comprising an end member comprising material for attenuating ultrasound.

3. A wheel probe as claimed in claim 2, wherein the end member has an extended portion thereof adapted to locate inside the rim of the wheel.

4. A wheel probe as claimed in claim 3, including sealing means locatable between the rim and the extended portion of the end member.

5. A wheel probe as claimed in any one of claims 2 to 4, wherein the mounting means further includes a support member which extends through the body and the end member and supports the annular mounting member within said chamber.

6. A wheel probe as claimed in claim 5, wherein the end member comprises polycarbonate material, or nylon.

7. A wheel probe as claimed in claim 6, wherein the rim has a portion of reduced diameter to reduce the width of contact between the rim and the component, and an elastomeric tire member located about the rim extends along said portion to attenuate unwanted ultrasound.

8. A wheel probe as claimed in claim 7, wherein the annular mounting member comprises polycarbonate material, or polythene or nylon.

* * * * *